United States Patent
Simmons et al.

(10) Patent No.: US 10,238,547 B2
(45) Date of Patent: Mar. 26, 2019

(54) PROPHYLACTIC DRESSING AND USE OF SAME IN THE PREVENTION OF INFECTION

(71) Applicant: GUI Global Products, Ltd., Houston, TX (US)

(72) Inventors: Kathleen A. Simmons, Houston, TX (US); Walter G. Mayfield, Houston, TX (US); Daniel M. Valdez, Kingwood, TX (US)

(73) Assignee: GUI GLOBAL PRODUCTS, LTD., Houston, TX (US)

( * ) Notice: Subject to any disclaimer, the term of this patent is extended or adjusted under 35 U.S.C. 154(b) by 623 days.

(21) Appl. No.: 14/671,320

(22) Filed: Mar. 27, 2015

(65) Prior Publication Data

US 2015/0351971 A1 Dec. 10, 2015

Related U.S. Application Data

(63) Continuation-in-part of application No. 14/295,814, filed on Jun. 4, 2014, now abandoned.
(Continued)

(51) Int. Cl.
*A61F 13/02* (2006.01)
*A61L 15/56* (2006.01)
(Continued)

(52) U.S. Cl.
CPC .... *A61F 13/0243* (2013.01); *A61F 13/00055* (2013.01); *A61F 13/025* (2013.01);
(Continued)

(58) Field of Classification Search
CPC ............ A61F 13/0243; A61F 13/00055; A61F 13/0233; A61F 13/0246; A61F 13/025; A61F 13/02; A61L 15/56; A61L 15/58
See application file for complete search history.

(56) References Cited

U.S. PATENT DOCUMENTS 3,675,654 A * 7/1972 Baker ............... A61F 13/42
604/361
3,918,446 A 11/1975 Buttaravoli
(Continued)

FOREIGN PATENT DOCUMENTS

CN        201295323    *   8/2009
CN        201295323 Y     8/2009
(Continued)

OTHER PUBLICATIONS

PCTUS2014040878—International Search Report dated Sep. 26, 2014.
EP Application No. 14807740.7—EP Search Report dated Dec. 20, 2016.

*Primary Examiner* — Ariana Zimbouski

(74) *Attorney, Agent, or Firm* — Mossman, Kumar & Tyler PC

(57) ABSTRACT

Wounds and temporary appliances can be protected against liquid contamination using a prophylactic dressing. The dressing includes a liquid resistant sheet and disposed thereon a first liquid barrier/adhesive strip and a second liquid barrier/adhesive strip wherein the first and second liquid barrier/adhesive strips are concentric; located at or near the periphery of the liquid resistant sheet; and are separated from one another by a gap. Adsorbent's and liquid indicators can be employed within the gap to add further functionality to the dressing. Also disclosed herein is a support useful for stabilizing leads to transcutaneous or percutaneous devices.

16 Claims, 5 Drawing Sheets

Related U.S. Application Data

(60) Provisional application No. 61/831,018, filed on Jun. 4, 2013.

(51) Int. Cl.
*A61L 15/58* (2006.01)
*A61F 13/00* (2006.01)
*A61M 25/02* (2006.01)

(52) U.S. Cl.
CPC ...... *A61F 13/0233* (2013.01); *A61F 13/0246* (2013.01); *A61L 15/56* (2013.01); *A61L 15/58* (2013.01); *A61F 2013/00217* (2013.01); *A61F 2013/00263* (2013.01); *A61M 2025/0253* (2013.01); *A61M 2025/0266* (2013.01)

(56) References Cited

U.S. PATENT DOCUMENTS

| | | |
|---|---|---|
| 4,040,427 A | 8/1977 | Winnie |
| 4,721,508 A * | 1/1988 | Burton ................ A61F 5/445 604/103.03 |
| 4,966,590 A | 10/1990 | Kalt |
| 5,607,388 A | 3/1997 | Ewall |
| 5,714,225 A * | 2/1998 | Hansen ................ A61F 5/443 424/443 |
| 6,206,864 B1 * | 3/2001 | Kavanagh ............ A61F 5/448 604/332 |
| 7,759,537 B2 | 7/2010 | Bishop et al. |
| 8,251,969 B2 * | 8/2012 | Van Den Bogart ..... A61F 13/82 604/385.17 |
| 2003/0056710 A1 * | 3/2003 | Radmacher ............ G01N 21/81 116/206 |
| 2005/0085795 A1 * | 4/2005 | Lockwood .......... A61M 1/0084 604/543 |
| 2006/0069362 A1 * | 3/2006 | Odorzynski ............ A61F 13/42 604/361 |
| 2007/0003606 A1 | 1/2007 | Booher |
| 2007/0078366 A1 * | 4/2007 | Haggstrom .......... A61F 13/0203 602/53 |
| 2008/0114276 A1 * | 5/2008 | Janusson ............... A61F 13/023 602/46 |
| 2009/0312685 A1 * | 12/2009 | Olsen .................... A61F 5/443 602/54 |
| 2010/0228113 A1 * | 9/2010 | Solosko ............... A61B 5/0416 600/382 |
| 2010/0294286 A1 | 11/2010 | Bellamy et al. |
| 2012/0016322 A1 * | 1/2012 | Coulthard ........... A61F 13/0216 604/319 |
| 2012/0302981 A1 * | 11/2012 | Lam ........................ A61F 5/445 604/344 |
| 2013/0150796 A1 * | 6/2013 | Souza ................... A61M 25/02 604/180 |
| 2015/0025436 A1 * | 1/2015 | Tang ..................... A61M 25/02 602/43 |

FOREIGN PATENT DOCUMENTS

| | | | |
|---|---|---|---|
| CN | 101658453 | * | 3/2010 |
| CN | 101658453 A | | 3/2010 |
| EP | 0236104 A3 | | 3/1987 |
| WO | 9415562 A1 | | 7/1994 |
| WO | 02/100639 A1 | | 12/2002 |

* cited by examiner

PROPHYLACTIC DRESSING AND USE OF SAME IN THE PREVENTION OF INFECTION

CROSS REFERENCE TO RELATED APPLICATIONS

This Application is a continuation in part of and claims priority from U.S. patent application Ser. No. 14/295,814, filed Jun. 4, 2014, which is incorporated herein by reference in its entirety and which further claims priority from U. S. Provisional Patent Application No. 61/831,018, filed on Jun. 4, 2013 and which is incorporated herein in its entirety by reference.

TECHNICAL FIELD

The present invention relates to a dressing. The present invention particularly relates to a dressing having prophylactic properties.

BACKGROUND

According to the Center for Disease Control, central line associated bloodstream infections result in thousands of deaths each year and billions of dollars in added costs to the U. S. healthcare system. Any transcutaneous or percutaneous medical device can lead to such infections. It would be desirable in the art treating wounds and caring for patients having transcutaneous or percutaneous devices to have a prophylactic dressing capable of preventing infection caused by contamination of the wound or the point where the medical device passes through the skin.

SUMMARY

In one aspect, the invention is a dressing comprising a liquid resistant sheet and disposed thereon a first liquid barrier/adhesive strip and a second liquid barrier/adhesive strip wherein the first and second liquid barrier/adhesive strips are concentric; located at or near the periphery of the liquid resistant sheet; and are separated from one another by a gap.

In another aspect, the invention is a method of protecting open wounds and transcutaneous or percutaneous devices from contamination comprising placing a dressing comprising a liquid resistant sheet and disposed thereon a first liquid barrier/adhesive strip and a second liquid barrier/adhesive strip wherein the first and second liquid barrier/adhesive strips are concentric; located at or near the periphery of the resistant sheet; and are separated from one another by a gap; over the wound or point of insertion of the transcutaneous or percutaneous device.

In still another aspect, the invention is a method of protecting open wounds and transcutaneous or percutaneous devices from contamination comprising placing a dressing comprising a liquid resistant sheet and disposed thereon a first liquid barrier/adhesive strip and a second liquid barrier/adhesive strip wherein the first and second liquid barrier/adhesive strips are concentric; located at or near the periphery of the liquid resistant sheet; and are separated from one another by a gap; and disposed within the gap is a liquid indicator; over the wound or point of insertion of the transcutaneous or percutaneous device and then periodically observing the liquid indicator to determine whether the first liquid barrier has been breached.

Another aspect of the invention is an adhesive sheet and affixed upon the side opposite the adhesive, a foam pad wherein the foam pad is configured to support the leads from a transcutaneous or percutaneous device.

It will be appreciated that the various Figures are not necessarily to scale and that certain features have been exaggerated for clarity and do not necessarily limit the features of the invention.

DETAILED DESCRIPTION

For the purposes of this application, the term "transcutaneous" means existing across the depth of the skin but also may mean passing through and into deeper tissues. The term "percutaneous" means made, done, or effected through the skin, such as using a needle. While not generally used interchangeably in the medical arts, for the purposes of this application, these terms are effectively synonyms because the dressings of this application may be used with any type of wound to the skin (except as noted below) as well as any opening into the body no matter how the wound or opening may have occurred. Similarly, the use of the term transcutaneous modifying a device or appliance also means including a percutaneous device or appliance.

Central line associated bloodstream infections result in thousands of deaths each year and billions of dollars in added costs to the U. S. healthcare system. Any transcutaneous or percutaneous medical device can lead to such infections. In addition to central line catheters, these infections may be caused by abdominal drains such as those used in liver transplants and hernia repair. Temporary devices used to assist other patients such as the so called left ventricular assistant devices (LVAD)s are of particular concern because they also very expensive and can be damaged by infections.

To improve the quality of life of patients with transcutaneous or percutaneous devices or even "slow to heal wounds," it is important to protect against infection caused by liquid infiltration. Such infiltration often occurs in mundane situation such as bathing, showering or other forms of ablution. For example an aseptic or antiseptic field around a wound can be compromised when water from a bath or shower passes into a dressing carrying with it harmful bacteria.

Figure 1:
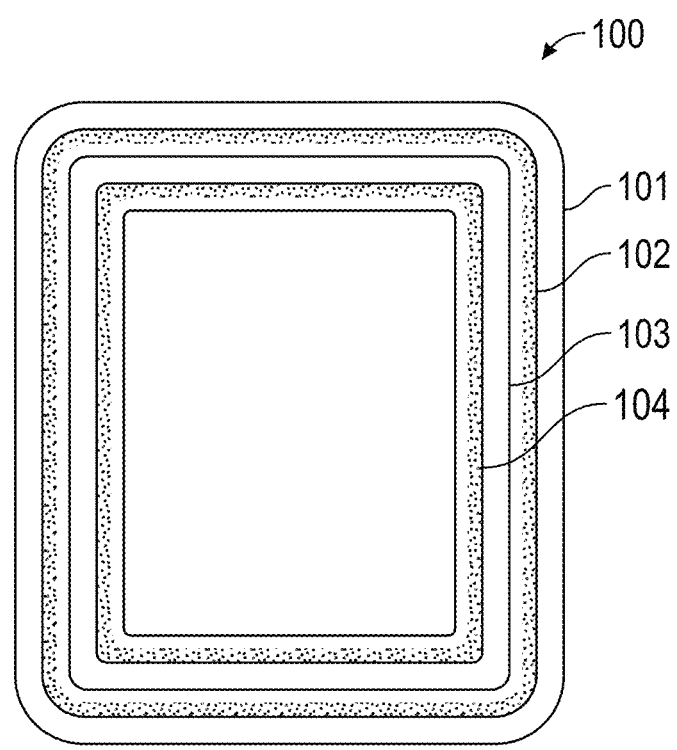
FIG. 1 is an illustration of a first embodiment of a dressing of the disclosure.

Employing a dressing of the disclosure can mitigate or prevent infiltration of environmental fluids into the wounds or insertion point of a transcutaneous or percutaneous device. Turning to FIG. 1, a first embodiment of a dressing (100) of the disclosure is illustrated wherein (101) is a liquid resistant sheet. The liquid resistant sheet may be completely impermeable but in some embodiments may pass vapor while precluding the passage of liquids (sometime referred in the art as being able to breathe). Such sheets may be of one or more layers. In some embodiments, the liquid resistant sheet may be prepared from a polymeric material. Any material known to be useful in preparing such liquid resistant sheets to those of ordinary skill in the art may be used with the method of the disclosure.

Disposed upon the liquid resistant sheet is a first liquid barrier/adhesive strip (102). The first liquid barrier/adhesive strip is located closest to the edge of the liquid resistant sheet. The liquid barrier functions to prevent infiltration of liquid under the dressing. Exemplary adhesives useful with the dressings of the disclosure include but are not limited to ALLEVYN™ from Smith & Nephew, Largo, Fla., and ELASTO GEL™ from Southwest Technologies, Inc., North Kansas City, Mo. Any adhesive known to those of ordinary skill in the art which are impermeable to liquids but also suitable for adhering a dressing to human skin may be employed in preparing the dressings of the disclosure.

Also shown in FIG. 1 is a second liquid barrier/adhesive strip (104). The second liquid barrier/adhesive strip is concentric with the first and they are separated from one another by a gap (103). The first and second liquid barrier/adhesive strip may be the same or different.

The gap between the first and second liquid barrier/adhesive strips is important. In one embodiment, the gap is filled with an adsorbent material. In another embodiment, the gap is filled with a liquid indicator. And in still another embodiment, the gap is filled with an absorbent also including a liquid indicator.

The use of an absorbent and/or a liquid indicator may permit for an extended period of prophylactic protection. When the gap is filled with an absorbent material, liquids that managed to infiltrate past the first liquid barrier/adhesive strip can be stopped by the absorbent materials for a period of time sufficient for the patient or the caregiver to perceive that the dressing has been compromised and should be replaced.

The use of a liquid indicator functions to make it easier to detect the infiltration of a liquid. The use of chromatic liquid indicators is especially useful as it allows for a very quick examination of the dressing. When the liquid indicator indicates that liquid has penetrated past the first liquid barrier/adhesive strip, the patient or a caregiver can make a ready determination that the dressing has been compromised and should be replaced.

The absorbent materials used with the method of the disclosure can be any known to be useful for preparing dressings. For example, in one embodiment a cellulose pad may be used. In another embodiment, a polymeric foam may be used for this purpose.

The liquid indicator may be any known to be useful to those of ordinary skill in the art of preparing dressings. It should be biologically benign and in some embodiments it may be hypoallergenic. While the indicator does not have to be a classical dye, if it is a dye and it is not proscribed for use on human skin, it may be used as long as it has a visible (chromatic) change in the presence of liquid water. In practicing the invention of the application, in some embodiments, the liquid indicator dye is a triarylmethane dye, a monoazo dye, a diazo dye, a xanthene dye, an anthraquinone dye, an indigoid dye, a quinoline dye, an FD&C dye, or a D&C dye. Such dyes useful with the present application include, but are not limited to: gentian violet, methylene blue, crystal violet, FD&C Yellow No. 5, FD&C Yellow No. 6, D&C Red NO. 17, FD&C Red No. 3, D&C Green No. 6, ethyl violet, brilliant green, FD&C Blue No. 2, D&C Yellow No. 1, FD&C Blue No. 1, or FD&C Green No. 3. In some embodiments, it is desirable that the indicator turn blue on contact with water.

In an alternative embodiment, the liquid indicator may be a material which changes color in the presence of a liquid, but does not require a chemical change to do so. For example, in one embodiment, the color change may be occur where a material which is opaque or translucent becomes more or even fully transparent in the presence of a liquid thereby allowing an obscured colored material to become more visible. The material may be in any form such as a powder or a fiber. One such material is silica gel. Another such material is cellulose, especially cellulose in the form of paper.

The dressings of the disclosure, especially when used with catheters and other transcutaneous or percutaneous devices may be composed of 2 parts. A first part that is applied either before the devices installed are also slipped underneath the lines leading from the device which functions to provide support to prevent rocking of the needle or catheter.

Figure 2A:
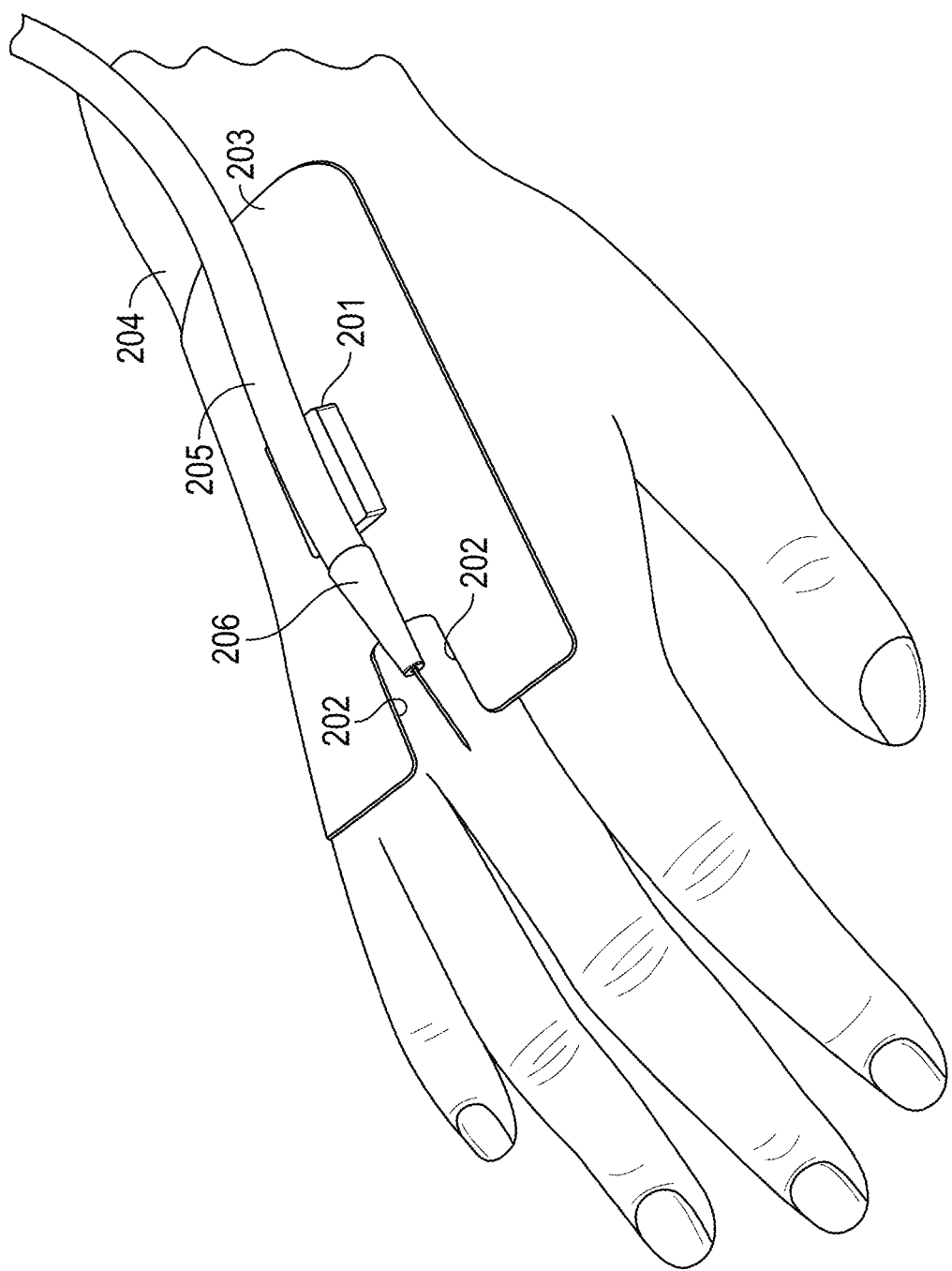
FIG. 2A illustrates a first part of an embodiment of a dressing configured to be used with a catheter or other temporary appliance.
Figure 2B:
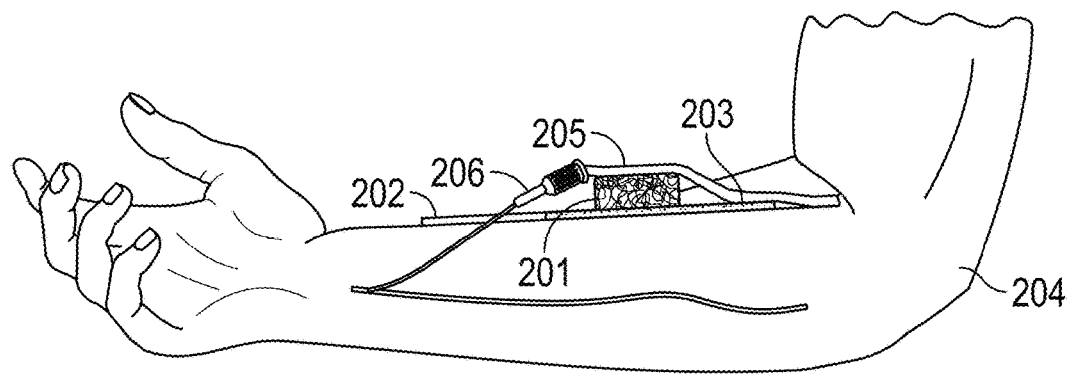
FIG. 2B illustrates the use of 2A with an IV.

Turning to FIGS. 2A & B, the bottom piece of a two-part dressing is shown at (203). In FIG. 2B, the bottom part of the dressing is in place on a patient, held in place by an adhesive covering most or all of the bottom of the bottom dressing. A foam block (201) which functions to stabilize movement of the line (205) leading from the appliance (in this case an IV (206)) and also functions to create a seal with the top part of the dressing such as is illustrated in FIG. 1. Note that there is a (202) that is sized to fit around the part of the appliance sitting on the surface of the patient (204). Beside stabilizing the needle are other part of the appliance, which reduces the amount of pain caused with movement of the line; the foam block allows the line to at least partially be submerged within the foam minimizing the amount of stretching required by the top of the dressing in order to make a liquid proof seal.

Figure 3:
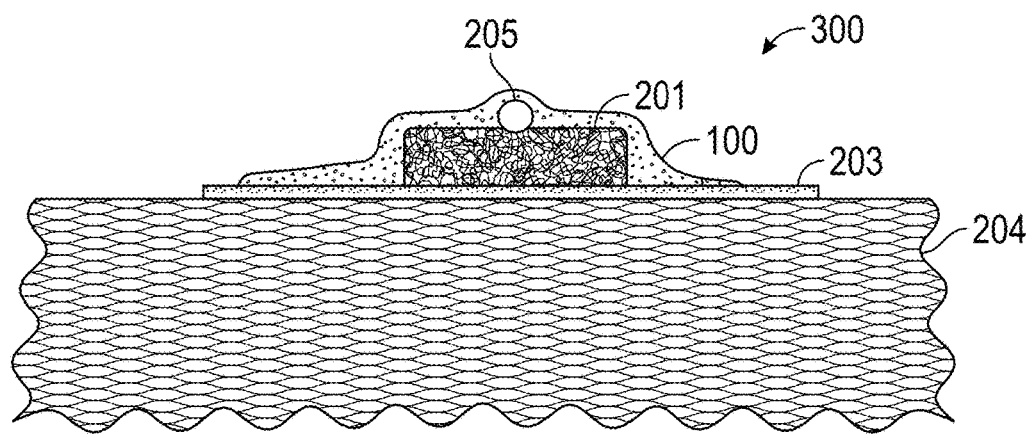
FIG. 3 is a side view of a lead foam support using a 2 part dressing.

Turning to FIG. 3, a two-part dressing of the disclosure (300) is shown in place on a patient (204). The bottom part of the dressing (203) including a foam pad (201) is illustrated wherein the foam pad both stabilizes the lead (205). The upper part of the dressing (100) is shown in place over the bottom part. It may be "baggy" or taut.

Figure 4:
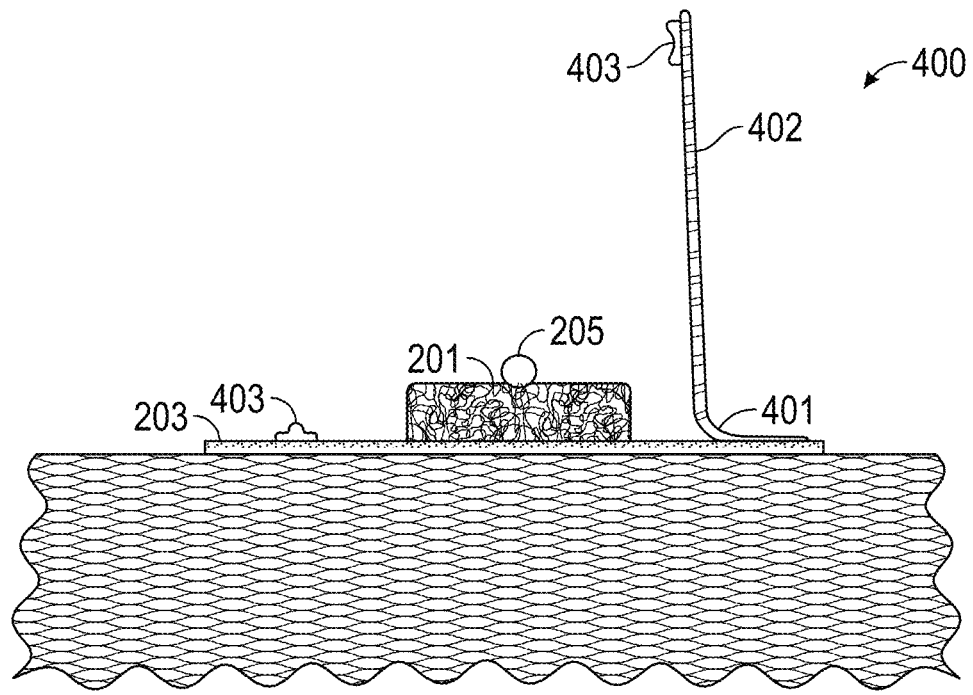
FIG. 4 is a side view of a lead foam support including a strap to hold the lead or leads in place.

In an alternative embodiment, the bottom part of the two part dressing can be used even without the top portion. Turning to FIG. 4, the bottom portion of the dressing illustrated in FIG. 3 is shown with additional elements. This new element is a strap (402) affixed adjacent to or on the base of the foam pad with reference number (401) illustrating an attachment of the strap to the dressing surface. Reference number (403) shows a two part hook and eye attachment that functions to hold the strap in a folded over configuration when the two components are brought together. A tacky or other form of adhesive may be used in place of the hook and eye. When folded over a lead or leads, the strap secures the leads in place on the foam pad and also prevents the leads from being lifted up causing the device attached to the leads to press down on a needle or the transcutaneous or percutaneous device.

Figure 5:
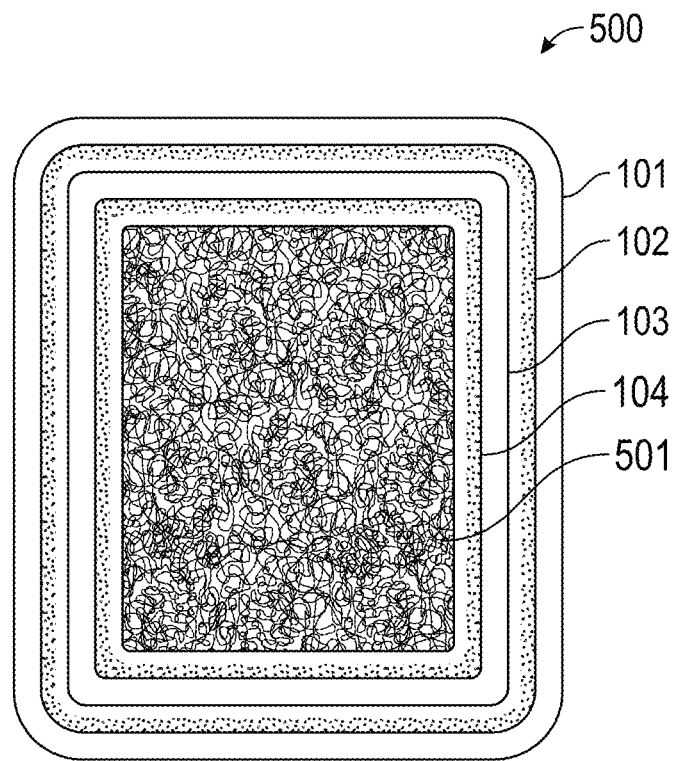
FIG. 5 is an illustration of an embodiment similar to that in FIG. 1 additionally comprising a surface treated to be resistant to sticking to a wound.

Turning now to FIG. 5, therein is illustrated an embodiment similar to that of FIG. 1 (500), but additionally comprising treating at least part of the dressing that would be in contact with a wound (501) with a composition that would prevent or at least reduce sticking. For example the part of the dressing in contact with the wound could be coated with or have integrated within it silica gel, or some other component to provide those properties. Any component that is safe for contact with a wound and which mitigate or prevent sticking to a wound may be used with the embodiments of the application. The area of non stick may encompass the entire inside surface of the dressing or it may be a narrow strip merely wide enough to cover at least part of the wound on which it is being used.

For the purpose of this application, the term lead or leads means an electrical wire or tubing for conveying a fluid, such as the line leading from an IV.

In alternative embodiments, the dressings of the disclosure can have separate apertures allowing for the exit of leads. Employment of antimicrobial elements is also within the scope of the disclosure. In one embodiment, the antimicrobial elements are delivered using a nano particle delivery system.

The dressings of the application are directed to the prevention of external liquid contamination of wounds or insertion points for transcutaneous or percutaneous devices. They are not suitable for use with wounds requiring maintaining a moist environment for the wounds. Exemplary of same would be ulcers and burns.

The dressings of the application are meant for temporary use. For example in some embodiments, they may be discarded after 5 days use. In other embodiments, they may be discarded after 2 days use. In still other embodiments, they may be used only to protect a patient for a single ablution and then discarded. They are also meant to be sized suitable for their intended applications with the dressing having dimensions suitable for its intended use.

Figure 6:
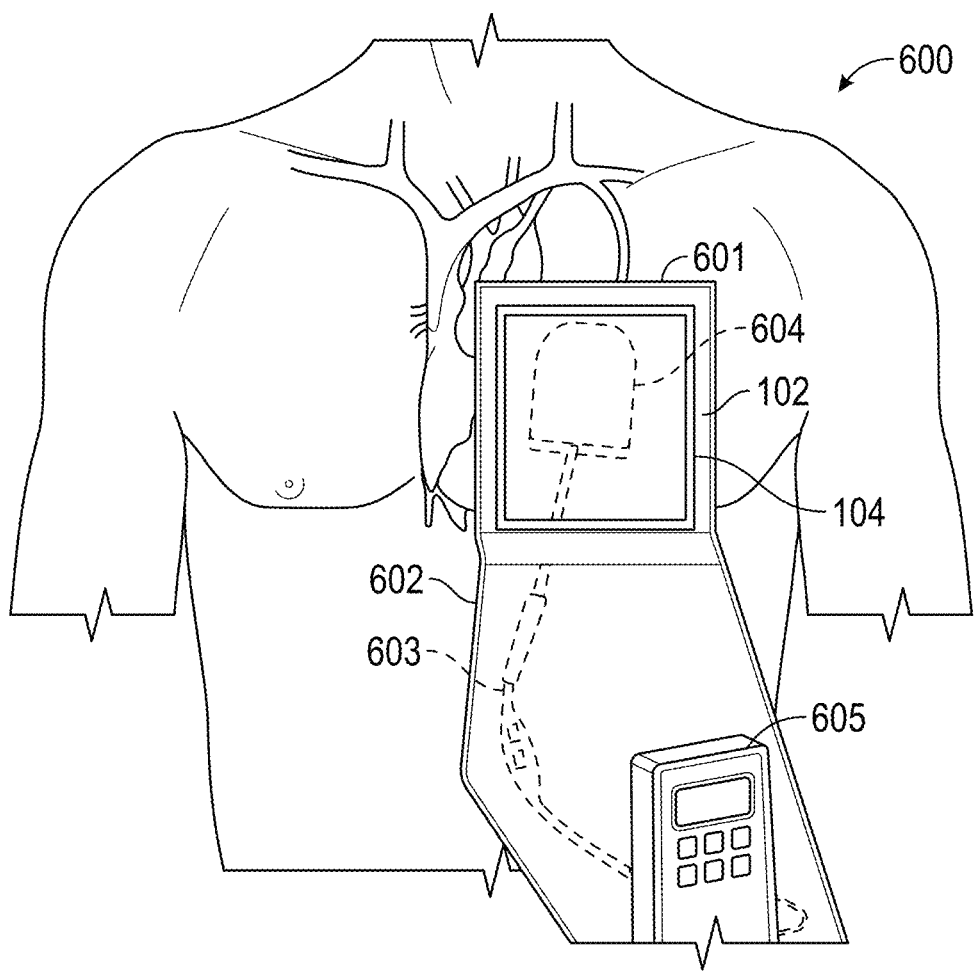
FIG. 6 is an illustration of the use of a dressing of the application configured to include a bag for inclusion of a the lead and monitor for an internal device.

Turning now to FIG. 6, a human torso (600) is shown. Thereon is an embodiment of a dressing of the application, the dressing being one meant specifically for bathing, especially showing is shown (601). A part of the dressing inside of the first liquid barrier/adhesive strip (102) and the second liquid barrier/adhesive strip (104) is adapted into a bag (602) for the leads (603) from an internal device (604) to an external controller (605). In addition to a bag, the dressing can be configured into other shapes to adapt to other devices. For example, in one embodiment, the dressing can be in the form of a tube to allow for a long lead to even exit the shower to equipment outside of the wash enclosure. A second element (803) can be used to seal around the long lead at a point either inside or outside of the tub.

Figure 7:
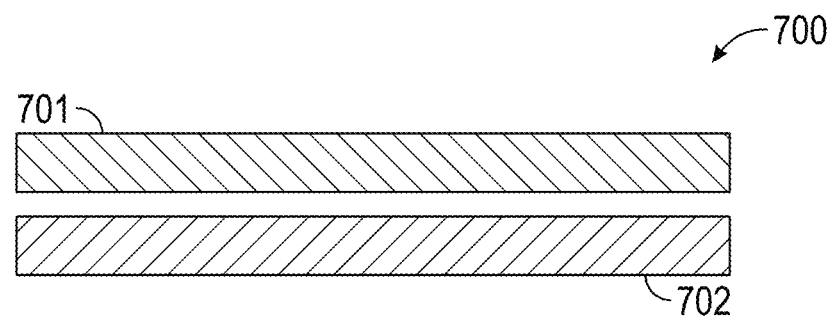
FIG. 7 is an illustration of a non-chemical liquid indicator of the application.

Turning now to FIG. 7, a liquid indicator which does not require a chemical change to show the presence of liquids, such as water (700) is illustrated. In this embodiment, the liquid indicator is composed of two parts. A first, non-colored part which is configured to be visible when a dressing of the application is being worn is shown (701). This first part is either opaque or translucent when dry and transparent or more translucent when wet with a liquid. The second part (702) has the characteristic of being colored when wet and optionally dry. When a liquid contacts the liquid indicator of this embodiment, it causes the first part to become transparent or more translucent allowing the second part to become more visible which is perceived by the eye as a color change.

For the purposed of this application, the term "color change" means both a change in the specific color such as changing from red to blue as occurs with a chemical change, or a change in the intensity of the color while remaining monochromatic. Further, where the liquid indicator is such that part of it may become dissociated with the dressing, such as a gauze or cellulose paper or fabric; it is desirable that such materials be used that they have the property of retaining their structural integrity when wet.

The dressings of the application may be prepared in any way known to be useful to those of ordinary skill in the art. For example, the adhesive is present in at least two strips with a gap in between. In one embodiment, the surface of the dressing to which the adhesive is to be applied can be treated with a first strip of adhesive and a space left without adhesive, and then a second of adhesive. In an alternative embodiment, the adhesive be applied to the entire surface with the gap created by the application of the liquid indicator. In some embodiments, the inner adhesive strip is present over the entire inner surface, including that part of the surface that is over the wound/burn/incision. In other embodiments, that surface does not include an adhesive.

In another embodiment, a second liquid indicator may be placed inside the inner concentric liquid barrier adhesive strip. The improvement of this embodiment is that it could be used to verify that even though the first barrier was breach by a liquid, the breaching liquid did not make it to the wound/burn/incision. This could be useful to physicians and nurse practitioners to determine whether prophylactic measures such as the use of antibiotics is necessary.

EXAMPLES

The following examples are provided to illustrate aspects of the invention. The examples are not intended to limit the scope of the invention and they should not be so interpreted.

Example 1

A prototype of a dressing substantially similar to that of FIG. 5 was applied to a human knee and submerged in water for about 5 minutes. No color change was observe indicating that no water had breached the first adhesive of the dressing.

Example 2

A prototype substantially similar to the prototype of Example 1 was placed upon a human knee in such a way that hair compromised the dressing at the outer barrier/adhesive strip (101). Water breached and came into contact with the color change indicator which in turn changed color indicating that the dressing had been compromised.

What is claimed:

1. A dressing comprising: a liquid resistant sheet and disposed directly thereon a first adhesive strip and a second adhesive strip wherein the first and second adhesive strips are concentric; located at or near the periphery of the liquid resistant sheet; and are separated from one another by a gap created by a liquid indicator, wherein the surface of the liquid resistant sheet across the gap between the liquid indicator and the liquid resistant sheet includes an adhesive; and the dressing is configured to indicate the infiltration of liquids from outside of the dressing.

2. The dressing of claim 1 wherein the liquid resistant sheet is completely impermeable.

3. The dressing of claim 1 wherein the liquid resistant sheet is able to pass vapor while precluding the passage of liquids.

4. The dressing of claim 1 wherein the liquid resistant sheet is of two or more layers.

5. The dressing of claim 1 wherein the liquid resistant sheet is prepared using a polymer.

6. The dressing of claim 1 wherein the first adhesive strip and the second adhesive strip comprise the same adhesive.

7. The dressing of claim 1 wherein the gap is created by an adsorbent material and a liquid indicator.

8. The dressing of claim 1 wherein the liquid indicator is a dye selected from the group consisting of: triarylmethane dye, a monoazo dye, a diazo dye, a xanthene dye, an anthraquinone dye, an indigoid dye, a quinoline dye, an FD&C dye, and a D&C dye.

9. The dressing of claim 1 wherein the liquid indicator is a material which changes color in the presence of a liquid, but does not require a chemical change to do so.

10. The dressing of claim 1 wherein at least a part of the dressing that will be in contact with a wound is treated with a composition to mitigate or stop the wound from sticking to the dressing.

11. A method of protecting open wounds and transcutaneous or percutaneous devices from contamination comprising placing a dressing of claim 1 over the wound or a point of insertion of the transcutaneous or percutaneous device.

12. A method of protecting open wounds and transcutaneous or percutaneous devices from contamination comprising:
    placing a a dressing of claim 1 over the wound or point of insertion of the transcutaneous or percutaneous device; and
    then periodically observing the liquid indicator to determine whether the first strip has been breached.

13. The method of claim 12 wherein the liquid indicator is a dye selected from the group consisting of: triarylmethane dye, a monoazo dye, a diazo dye, a xanthene dye, an anthraquinone dye, an indigoid dye, a quinoline dye, an FD&C dye, and a D&C dye.

14. The method of claim 12 wherein the dressing is exposed to liquid infiltration during bathing, showering, or other forms of ablution.

15. The dressing of claim 1 wherein an adhesive is applied to an entire surface of the dressing.

16. The dressing of claim 1 wherein an adhesive is not applied across an area away from the periphery of the liquid resistant sheet.

* * * * *